US00PP08306P

United States Patent [19]

Schumann

[11] Patent Number: Plant 8,306

[45] Date of Patent: Jul. 13, 1993

[54] GERANIUM PLANT NAMED FISBING

[75] Inventor: Ingeborg Schumann, Münster, Fed. Rep. of Germany

[73] Assignee: Florfis AG, Binningen, Switzerland

[21] Appl. No.: 779,296

[22] Filed: Oct. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Attorney, Agent, or Firm*—Foley & Lardner

[57] ABSTRACT

A new and distinct cultivar of geranium named Fisbing, particularly characterized by the combined features of light red double flowers, vigorous growth and well branched habit, and deep green foliage with medium brown zonation.

1 Drawing Sheet

The present invention comprises a new and distinct cultivar of geranium, botanically known as *Pelargonium peltatum L'Hert*, and hereinafter referred to by the cultivar name Fisbing.

Fisbing is a product of planned breeding program which had the objective of creating new ivy geranium cultivars with red flower color, foliage with zonation, and vigorous growth.

Fisbing was originated from a hybridization made by the inventor Ingeborg Schumann in a controlled breeding program in Galdar, Gran Canaria, Spain in 1986. The female parent was a hybrid seedling, derived from crossing a hybrid resulting from a cross between the cultivars Pelenberger and Tavira, with the cultivar Guimalo (known also by trademark "Cocorico"), all of which have red colored flowers and vigorous growth. The male parent of Fisbing was Admiral Bouvet, characterized by its light red double flowers, bushy plant habit and strong zonation.

Fisbing was discovered and selected as one flowering plant within the progeny of the stated cross by Ingeborg Schumann in May 1987 in a controlled environment in Galdar, Gran Canaria, Spain.

The first act of asexual reproduction of Fisbing was accomplished when vegetative cuttings were taken from the initial selection in February 1988 in a controlled environment in Hillscheid, Federal Republic of Germany by, or under the supervision of, Ingeborg Schumann.

Horticultural examination of rooted cuttings initiated in 1988 and continuing thereafter has demonstrated that the combination of characteristics as herein disclosed for Fisbing are firmly fixed and are retained through successive generations of asexual reproduction.

Fisbing has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fisbing, which in combination distinguish this geranium as a new and distinct cultivar:

1. Red double flowers
2. Semi-circular shaped umbels

3. Comparatively dark green foliage with brown zonation with zonation nearly disappearing in summer
4. Late flower response in spring
5. Vigorous growth and well branched plant habit Of the many commercial cultivars known to the present inventor, the most similar in comparison to Fisbing are the parent varieties Tavira and Admiral Bouvet. Reference is made to attached Chart A which compares certain characteristics of Fisbing to those same characteristics of Tavira and Admiral Bouvet. In general comparison Fisbing has a light red flower color, while Admiral Bouvet has orange red colored flowers and Tavira is carmine red. The leaves of Fisbing are deeper green than those of the comparison varieties, without any tendency to yellow. Fisbing has a more vigorous growth than Admiral Bouvet and better branching characteristics than Tavira.

The accompanying color photographic drawing comprises a side elevational view showing typical flower and foliage characteristics of Fisbing, with colors being as true as possible with illustrations of this type. The photograph was taken in the summer when brown zonation nearly disappears.

In the following description color references are made to the Royal Horticultural Society Color Chart. The color values were determined indoors from flowers taken from plants grown outdoors in June at Hillscheid, Federal Republic of Germany.

Classification:

*Botanical.*—A hybrid of the species *Pelargonium peltatum L'Hert.*

*Commercial.*—Ivy geranium, cv. Fisbing.

INFLORESCENCE

A. Umbel:

*Average diameter.*—76 mm.
*Average depth.*—45 mm.
*Peduncle length.*—148 mm.
*Pedicel length.*—25 mm.
*Pedicel color.*—Green, no anthocyanin.
*Number of flowers per umbel.*—7.3.

B. Corolla:

*Average diameter.*—44 mm.
*Form.*—Double.
*Number of petals.*—17–23.
*Color (general tonality from a distance of three meters).*—Light red.

*Color of upper surface of petals.*—R.H.S. 46C, no noticeable fading.

*Color of lower surface of petals.*—R.H.S. 55A-B, pink.

*White zone at the base of petal.*—Present, small white throat in center.

*Color of sepals.*—Green, no anthocyanin.

*Petaloids.*—There is average of two or three small petals with a stamen on top; petaloids are essentially transformed anthers.

C. Bud:

*Shape.*—Round, pointed.

*Color (sepals).*—Light green.

*Color (tips of petals).*—White with red margin, later entirely red.

D. Reproductive organs:

*Androecium.*—3–6 anthers, not all of which are fertile, with orange pollen.

*Gynoecium.*—6–7 lobed stigma.

E. Spring flowering response period: In Hillscheid, Federal Republic of Germany, in 1989 10% of plants with at least 1 flower opened 11 weeks after planting of unrooted cuttings.

F. Outdoor flower production: The flower count in 1989 in Hillscheid, Federal Republic of Germany indicated between 130 and 140 flowers per plant for May through September observation period.

G. Durability: Good rain resistance. No shattering.

H. Seed production: Fisbing has low fertility; practically no seed is set after pollination.

PLANT

A. Foliage:

*Form.*—Ivy shaped.

*Margin.*—Entire.

*Color (upper surface).*—Medium to dark green, approximately 137A-B.

*Color (zonation).*—Brown, ring-shaped approximately R.H.S. 166A; strong in spring, hardly visible in summer.

*Tolerance of botrytis.*—Good.

B. General appearance and form:

*Internode length.*—4–6 cm.

*Branching pattern.*—6.8 branches after 12 weeks of growing time.

*Length of branches.*—About 35 cm (16 week old plants, in June).

CHART A

| | FISBING | TAVIRA | A. BOUVET |
|---|---|---|---|
| Flowering color | light red 46C | carmine 52A | orange red 43B |
| Zonation on leaf | medium | absent | strong |
| Growth habit | vigorous, bushy | vigorous, loose | compact, bushy |
| Branching habit (number of branches) | 6.8 | 4.2 | 5.5 |
| Beginning of flowering (% of flowering plants in 11th week) | 10% | 50% | 40% |
| Number of umbels | 136 | 99 | 129 |
| Internodes | 4–6 cm | 5–7 cm | 3–5 cm |

I claim:

1. A new and distinct cultivar of geranium plant named Fisbing, as illustrated and described.

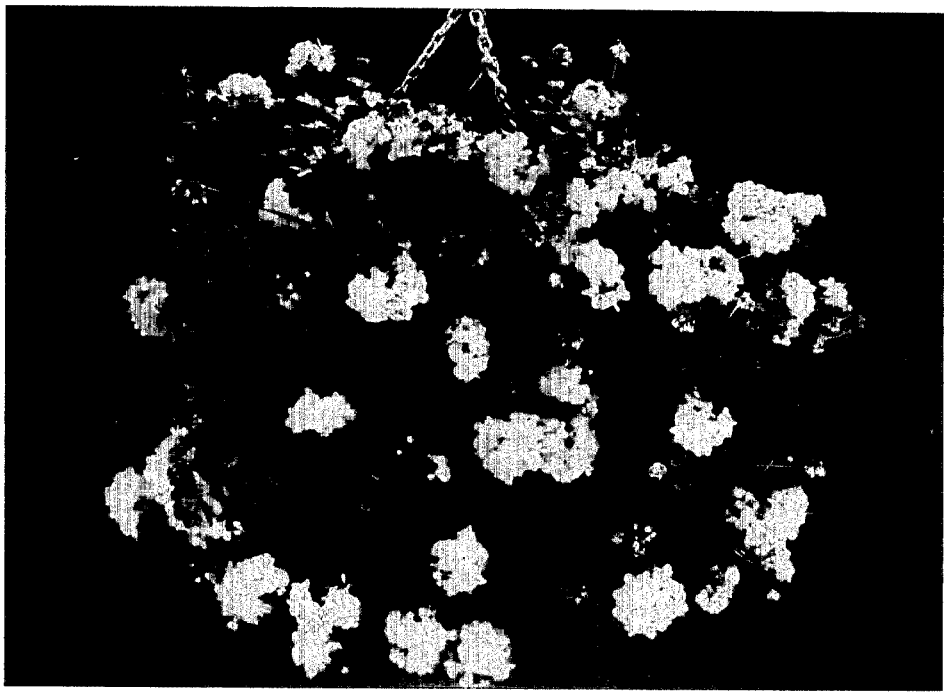

* * * * *